United States Patent [19]
Holbrook et al.

[11] Patent Number: 5,224,769
[45] Date of Patent: Jul. 6, 1993

[54] METHOD AND DEVICE FOR NON-INVASIVE MONITORING OF HYDRATION STATE OF PLANTS

[75] Inventors: Noel M. Holbrook, Palo Alto; Michael J. Burns, Mountain View, both of Calif.

[73] Assignee: University of Florida, Gainesville, Fla.

[21] Appl. No.: 816,737

[22] Filed: Jan. 3, 1992

[51] Int. Cl.⁵ .................. G01R 19/00; A01G 25/16
[52] U.S. Cl. .................... 47/48.5; 324/664; 47/48.5
[58] Field of Search ............ 47/48.5, 79, 58, 1.01; 324/664, 667

[56] References Cited

U.S. PATENT DOCUMENTS

| | | | |
|---|---|---|---|
| 3,081,429 | 3/1963 | Moe | 324/667 |
| 4,616,425 | 10/1986 | Burns | 324/667 |
| 4,638,594 | 11/1987 | Huguet et al. | 47/48.5 |
| 4,683,904 | 8/1987 | Iltis | 324/667 |
| 4,864,850 | 9/1989 | Price | 324/664 |

Primary Examiner—Carl D. Friedman
Assistant Examiner—Michele A. Van Patten
Attorney, Agent, or Firm—Kerkam, Stowell, Kondracki & Clarke

[57] ABSTRACT

A system for the non-invasive monitoring of the hydration state of a plant comprising the elements:

a timing capacitor comprising a plurality of conductive elements adapted for mounting on a plant part to sense the hydration state capacitance of the plant part;

a capacitance-to-frequency converter electrically connected to the timing capacitor comprising an oscillator circuit having a frequency dependent upon the value of the timing capacitor and independent of the electrical losses in said timing capacitor;

means for supplying electrical power to the capacitance-to-frequency converter;

means for measuring the frequency generated by the capacitance-to-frequency converter, the frequency bearing a known relationship to the dielectric constant and, hence, the water content of the plant part; and devices for electrically guarding the circuit generated by the elements from capacitance extraneous to the plant part comprising means for surrounding the elements with shields of electrical potential substantially equal to that of the timing capacitor.

11 Claims, 4 Drawing Sheets

METHOD AND DEVICE FOR NON-INVASIVE MONITORING OF HYDRATION STATE OF PLANTS

BACKGROUND OF THE INVENTION

1. Field of the Invention

The present invention relates to a novel device and system for the non-invasive monitoring of the water content of a living plant.

2. Description of the Prior Art

Many fruit crops, particularly citrus, show a correlation between their resistance to frost damage in winter and their hydration states of the previous summer. Devices which would be used to monitor commercial orchards to provide the farmer with information, particularly during times of drought, with an instant reading on the hydration state of the trees would be extremely valuable to the industry. Such information would not only allow the farmer to schedule irrigation to conserve water and use it more efficiently, but would allow the farmer to "tune" the hydration state of his orchard in summer to produce the desired frost-resistance for the following winter.

Information concerning the water content of large trees is also invaluable to commercial companies that specialize in transplanting large trees. These companies usually warrant the transplanted tree for periods ranging up to one year after the transplant. The act of transplanting a large tree creates considerable stress on the tree due to the injury or removal of large portions of the tree's root system. This usually hinders the tree's ability to remove water out of the soil, thus making the tree very susceptible to drying out. Therefore, an inexpensive and easy way of monitoring the tree's hydration state can allow the caretakers to give a greater amount of attention to those trees in need and would provide an economical way of verifying that the customer did not neglect the trees during the warranty period.

Although knowledge of the moisture status of the soil-plant system is essential for the study of plant water relations, techniques for the determination of the water content of both soils and plant tissues continue to be questioned [Gardner, "Water content: an overview," Int. Conf. on Measurement of Soil and Plant Water Status, Utah State Univ., Logan, Utah, 1:7-9 (1987); and Kramer, "Plant relative water content and related methods: Historical perspectives and current concerns," Int. Conf. on Measurement of Soil and Plant Water Status, Utah State Univ., Logan, Utah, 2:1-8 (1987). Existing techniques for the measurement of plant moisture content can be criticized as insensitive, inaccurate or indirect. What is required is an inexpensive, readily automated, portable technique that is sensitive to changes in water content while being insensitive to the character of the matrix [Gardner, supra].

Stem water contents are difficult to determine because of high levels of hydration, geometrical constraints and potentially deleterious effects of intrusions into living tissues. Changes in stem diameter [Hinckley et al, "Temporal and spatial variations in the water status of forest trees," Forest Science Monograph 20 (1978)], extraction of tissue cores [Waring et al, "Sapwood water storage: its contribution to transpiration and effect upon water conductance through the stems of old-growth Douglas-fir," Plant, Cell and Environment, Vol. 1, pages 131-140 (1978); and Waring et al, "The contribution of stored water to transpiration in Scots pine," Plant, Cell and Environment, Vol. 2, pages 309-317 (1979)], tissue water potential [Goldstein et al, "Influence of insulating dead leaves and low temperatures on water balance in an Andean giant rosette plant," Plant, Cell and Environment, Vol. 6, pages 649-656 (1983); and Nobel et al, "Transpiration stream of desert species: resistances and capacitances for a $C_3$, a $C_4$ and a CAM plant," Journal of Experimental Botany, Vol. 34, pages 1379-1391 (1983)], and gamma ray attenuation [Edwards et al, "A method for measuring radial differences in water content of intact tree stems by attenuation of gamma radiation," Plant, Cell and Environment, Vol. 6, pages 255-260 (1983); and Brough et al, "Diurnal changes in water content of the stems of apple trees, as influenced by irrigation," Plant, Cell and Environment, Vol. 9, pages 1-7 (1986)] have all been used to monitor changes in stem moisture content. Dimensional changes are both easily automated and non-destructive, but are sensitive only to water content changes in the extracambial elastic region of the stem. In the case of palms, the existence of a relatively stiff outer layer surrounding the living, elastic tissues [Tomlinson, "Anatomy of the Monocotyledons: I. Palmae" (1961)] renders this technique unsatisfactory. Stem tissue, extracted using an increment borer, samples the entire cross-section, but the technique is destructive and may alter the water content of the sample due to tissue compression [Holbrook, "The role of stem water storage in the arborescent palm, Sabal palmetto," M. Sc. Thesis, University of Florida, Gainesville, Fla. (1989)]. Psychrometers inserted into stems have several disadvantages, including local tissue damage, release of cell contents into the apoplast during insertion, temperature fluctuations and calibration difficulties. Gamma ray attenuation avoids many of these problems, but its application is complicated by safety considerations.

Another approach to monitoring tissue moisture status is to measure the dielectric constant. The dielectric constant ($\epsilon$) is an intrinsic property of a material and relates to the ability of a material to store electrical energy reversibly. The dielectric constant ($\epsilon$) is defined as:

$$\epsilon = 1 + X \qquad (1)$$

where X is the electrical susceptibility—the proportionality constant between the electric field and the degree of polarization [Jackson, Classical Electrodynamics, John Wiley & Sons, New York (1975)]. Because of its large dipole moment and ability to form hydrogen bonds, water has an extremely high dielectric constant (78.3 at 25° C.) compared to most solids and liquids (3 to 10) [Wheast, Handbook of Chemistry and Physics, CRC Press, Cleveland, OH (1975)]. Furthermore, the dielectric properties of pure water are fairly insensitive to temperature (approximately $-0.37°$ C.$^{-1}$ from 10° to 30° C.) [Wheast, supra] and independent of frequency up to $10^{10}$ Hz [Jackson, supra]. Although solutes do affect the dielectric properties of an aqueous medium, at low concentrations and high frequencies this influence is thought to be small [Hasted, Aqueous Dielectrics, Chapman and Hall, London (1973)]. Changes in the apparent dielectric constant of a water-permeated medium, therefore, may result from primarily changes in the moisture content [Sheriff, "An apparatus for the measurement of leaf dielectric properties in the high frequency region," Journal of Experimental Botany, Vol.

27, pages 645-650 (1976); Topp et al, "Electromagnetic determination of soil water content: measurements in coaxial transmission lines," *Water Resources Research,* Vol. 16, pages 574-582 (1980); and Pissis et al, "A dielectric study of the state of water in plant stems," *Journal of Experimental Botany,* Vol. 38, pages 1528-1540 (1987)].

Dielectric measurements can be made in both the frequency and time-domain [Hasted, supra]. Both approaches have been used to determine plant and soil moisture with varying degrees of success [Sheriff, supra; Dalton et al, "Time-domain reflectometry: simultaneous measurement of soil water content and electrical conductivity with a single probe," *Science,* Vol. 224, pages 989-990 (1984); Halbertsma et al, "Application and accuracy of a dielectric soil water content meter," Proc. Int. Conf. Measurement Soil Plant Water Status, 1:11-15 (1987); Topp, "The application of time-domain reflectometry (TDR) to soil water content measurement," Proc. Int. Conf. Soil Plant Water Status, 1:85-93 (1987); and Harbinson et al, "The use of microwaves to monitor the freezing and thawing of water in plants," *Journal of Experimental Botany,* Vol. 38, pages 1325-1335 (1987)].

Sheriff [supra] uses a primitive radio-frequency oscillator (about 25 MHz) to measure the capacitance of a capacitor formed by two plates with a leaf and some remaining air forming a dielectric layer. He then measured the effective dielectric constant of this layered system and calculated (knowing the textbook value for air being 1) the dielectric constant of his leaf. Sheriff's apparatus uses two plates of fixed position as opposed to plates designed to be completely in contact with the plant. The apparatus measures the total capacitance of the capacitor plates. This includes their capacitance coupling to objects outside the plates. This means that zeroing the apparatus is necessary before use and not altering the local environment (e.g., placement of nearby laboratory objects) during measurements is critical. For example, the movement of a hand near the apparatus while taking a measurement would result in the apparatus "seeing" the hand as well as the leaf under study. This has been a nuisance that has restricted the wide application of this technique.

U.S. Pat. No. 4,114,090 to Poskitt does form a type of dielectric capacitor with the sample (in this case, tobacco leaves) forming the dielectric between the capacitor plates. This capacitor forms part of an oscillator circuit whose frequency depends on the capacitance of the capacitor (10) and on the value of the resistors (11 and 12). However, since the patent does not describe how the oscillator works, one cannot assess whether the device will, in addition to responding to the dielectric constant of the leaves (assumed to be due to moisture), give erroneous readings due to changes in the conductivity of the leaves. Actually, the aforementioned patents are either obviously susceptible to giving erroneous readings due to conductivity changes in the materials under test or the patent does not give enough details to determine whether the circuit will give erroneous readings. Conductivity changes would usually come about in the materials due to changes in ion concentrations ("saltiness") due to evaporation of water, due to the chemistry of the material, or due to its history. For example, sponge soaked in salt water has a high conductivity (about $10^{-1}$ mhos/cm), one soaked in distilled water a low conductivity (about $10^{-6}$ mhos/cm) Yet they have the same dielectric constant and so all devices using dielectric measurements to read moisture content should give the same reading. A truly valuable device would be one that is not fooled by the conductivity difference.

Sheriff and Poskitt were using dielectric sensing which is susceptible to errors due to influences of objects near, but not in, the "sensing" region of the capacitor sensors due to fringe fields. This has been another traditional problem associated with all types of capacitance sensors.

It is an object of the present invention to provide a non-invasive system for monitoring the hydration state of plants which is not subject to the above-noted prior art disadvantages.

More particularly, it is an object of the present invention to provide such a system which is able to actively suppress the fringe fields for the inner "sensing" region of the sensors, i.e., a system which would ensure that external influences such as people or animals in contact with the plant would not give false readings.

SUMMARY OF THE INVENTION

The above and other objects are realized by the present invention, one embodiment of which provides a system for the non-invasive monitoring of the hydration state of a plant comprising the elements:

a timing capacitor comprising a plurality of conductive elements adapted for mounting on a plant part to sense the hydration state capacitance of the plant part;

a capacitance-to-frequency converter electrically connected to the timing capacitor comprising an oscillator circuit having a frequency dependent upon the value of the timing capacitor and independent of the electrical losses in said timing capacitor;

means for supplying electrical power to the capacitance-to-frequency converter;

means for measuring the frequency generated by the capacitance-to-frequency converter, the frequency bearing a known relationship to the dielectric constant and, hence, the water content of the plant part; and devices for electrically guarding the circuit generated by the elements from capacitance extraneous to the plant part comprising means for surrounding the elements with shields of electrical potential substantially equal to that of the timing capacitor.

DETAILED DESCRIPTION OF THE INVENTION

The invention is illustrated by the following non-limiting description of an application of the system to the measurement of the hydration state of potted individual *Sabal palmetto* plants.

Details regarding tree cultivation under greenhouse conditions, as well as results of water balance experiments with these trees, are described by Holbrook and Sinclair ["Water balance in the arborescent palm, *Sabal palmetto*: Transpiration and stem water storage," *Plant, Cell and Environment* (1992)].

Figure 1:
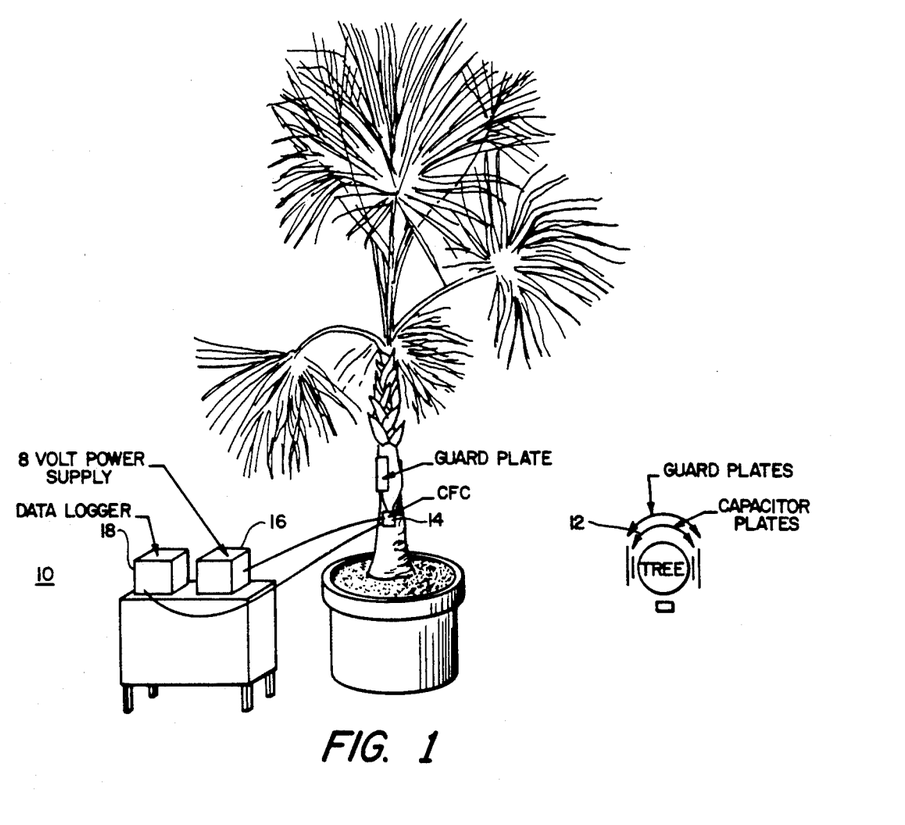
FIG. 1 is a schematic drawing of the device of the invention used to monitor stem capacitance. The paired copper plates 12 are located flush with the exterior of the trunk. The capacitance-to-frequency converter (CFC) box 14 is located just below the bottom edge of the timing plates. An 8 V supply 16 (floating ground) powers the CFC and frequency is recorded using a data-logger 18. The inset shows a cross-section of the tree stem with capacitor plates drawn to scale.
Figure 2:
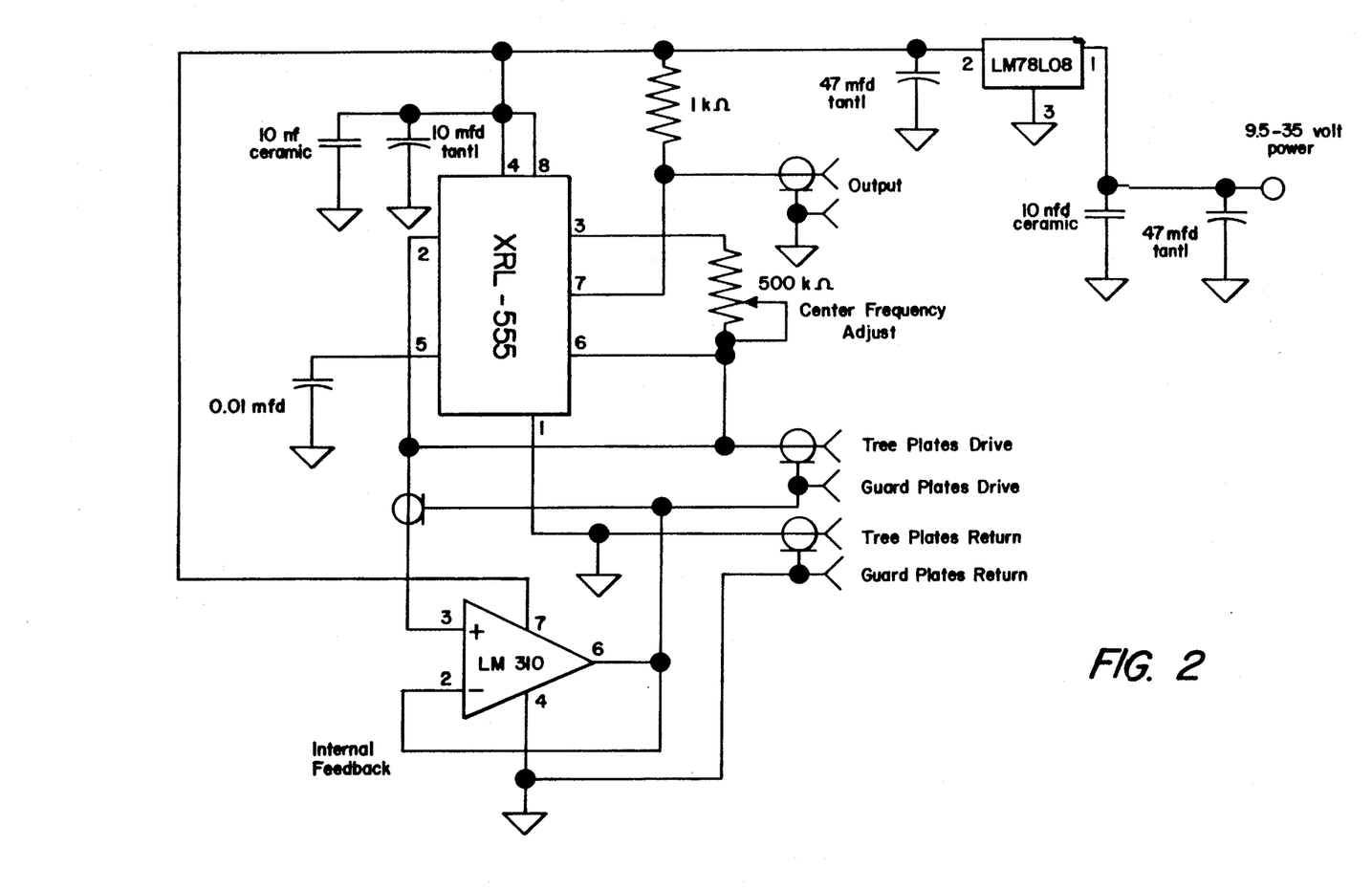
FIG. 2 is a diagram of an example of the capacitance-to-frequency (CFC) circuit of the invention.

Frequency-domain measurements of stem capacitance were made using a capacitance-to-frequency converter (CFC). The CFC consisted of an oscillating circuit sealed in a water-tight metal case with a frequency that depended upon the value of a large parallel plate capacitor that surrounded the stem (FIG. 1). The circuit was supplied with a fixed voltage (8 V) and the frequency of the oscillator was allowed to vary so that the circuit remained in resonance (i.e., voltage and current completely out of phase). The heart of the circuit consisted of a timer chip (LM555) operating in an astable mode [Jung, *IC Timer Cookbook*, Howard W. Sams & Co., Indianapolis, Ind. (1977); FIG. 2]. Frequency was measured using a data-logger (Model 21X, Campbell Scientific) as a high-frequency pulse counter. Pulses were summed at 1 s intervals and a mean value recorded at 15 or 30 minute intervals. Air temperature was measured with a chromel-alumel thermocouple and the voltage from the thermocouple recorded at 15 minute intervals by the data-logger.

Optimally, a conventional voltage regulator device, i.e., a chip (e.g., LM78L08) to supply a constant voltage to power the XRL-555 (a 555 clone) and extra filter capacitors to increase the stability of the power supply may be added to the circuit. These enable the use of the device under conditions where conventional electrical power is unavailable, e.g., car batteries may be utilized as the power source. As battery voltage runs down, the 555 chip will function (with an error of 0.15%/volt of battery drift) until the power supply drops to 4 volts, at which point the chip starts to malfunction. If the car batteries started at 12–14 volts, this can introduce an error of as much as 1.5% in the reading by the time the chip starts to totally malfunction from the lack of power. Of course, as the supply voltage drops, the errors actually are much larger since the LM310 starts malfunctioning sooner (around 5 volts), and so the guard voltage on the plates starts to fail. If one does not know the status of the batteries (e.g., the CFC is running for several weeks in an orchard), then one cannot tell if a strange measurement is real or if it is due to the batteries running down. The added voltage regulator chip solves this problem.

The voltage regulator chip does two things: 1) It produces a constant 8 volt output to power the LM555 and LM310 as long as its own supply is between 9.5 and 35 volts. The output of the LM78L08 will drift by 0.002 volt/volt of power supply drift (0.014%/volt of power supply drift). This means that using a LM78L08 to power the LM555 chip reduces the timing error of the LM78L08-LM555 combination to 0.0003%/volt of power supply drift from its value of 0.15%/volt of power supply drift for the LM555 alone. 2) The LM78L08 has the additional feature that it will turn off the rest of the CFC circuit if its power supply voltage drops below 9.5 volts. This means that if the CFC is being powered by batteries, then rather than allow the introduction of errors into the CFC measurements as the batteries wear down, it will simply turn the LM555 and LM310 off. The advantage of this is that, for example, if the CFC were left unattended for long periods of time, one would not need to guess when it started to produce erroneous measurements due to the batteries dying. Instead, this newer CFC circuit will take valid measurements when there is sufficient power, or it will take no measurements at all.

It will be understood by those skilled in the art that it is not critical to the practice of the invention to employ a LM555 chip. It was used in the example described herein because it allowed the design of a "resonating circuit," i.e., one which resonates independently of the losses in the timing capacitor. Thus, any device which permits the creation of a current resonance rather than a charge resonance so that the measurements are not "fooled" by ionic changes (hence conductivity changes in the plant tissue may be employed.

Oscillation frequency is determined by the time required to charge or discharge a "timing" capacitor between ⅓ and ⅔ of the supply voltage ($V_2$). The timing capacitor consisted of two copper plates (6.3×30.5 cm, <0.2 cm thick) mounted vertically on opposite sides of the tree stem (FIG. 1). The sides of the tree were smoothed with a belt sander so that the copper plates would lie flush against the stem. The side of the copper plates adjacent to the stem was coated with Kapton polyimide film (Dupont Company, Wilmington, Del.) to prevent any electrochemical interactions between plates and tree. Any change in the value of the capacitor formed by the copper plates alters the time needed for charge and discharge and hence alters the resonant frequency. As the capacitance increases, oscillator frequency decreases, and vice versa. The circuit was configured to charge and discharge the capacitor through the same resistor ($R_2$) and hence operated with an intrinsic 50% duty cycle [Jung, supra]. Before sealing the water-tight boxes, $R_2$ was adjusted so that all CFC circuits resonated within 0.1 Hz when connected to the sam test capacitor. The output to the pulse counter was a comparator (a transistor to ground internal to the LM555) tied high via a 1 kΩ resistor so the output was either at $V_2$ (when the capacitor was charging) or at 0 V (when discharging).

Figure 3:
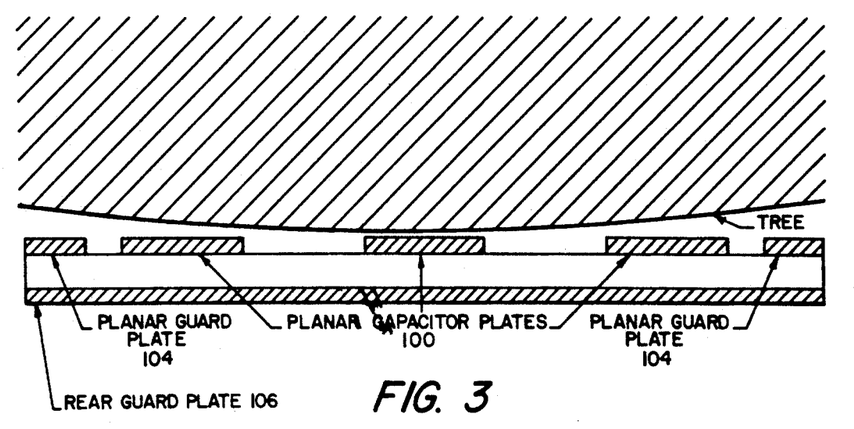
FIG. 3 is a schematic drawing of the device of the invention wherein the capacitor plates 100 are positioned on the same side of the plant 102 and the guard plates 104 are positioned outside of the capacitor plates 100. A rear guard plate 106 is also provided. This arrangement is particularly suitable for measuring the hydration state of plants by affixing the plates on the underside of leaves of the plants without blocking out sunlight.
Figure 3A:
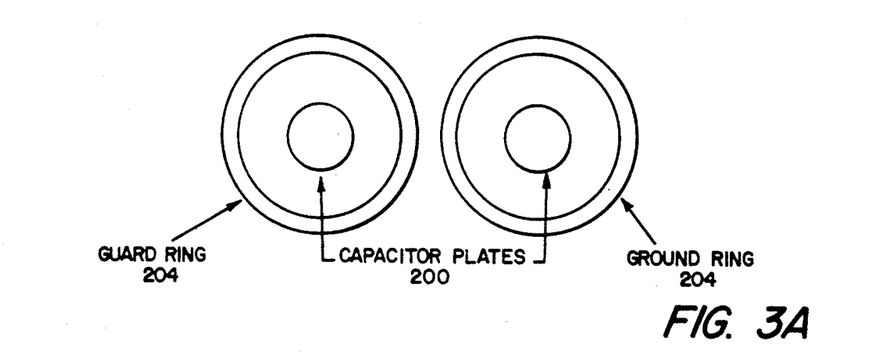
FIG. 3A is a schematic end view showing the relationship of the capacitor plates 200 and their coaxial guard rings 204.
Figure 3B:
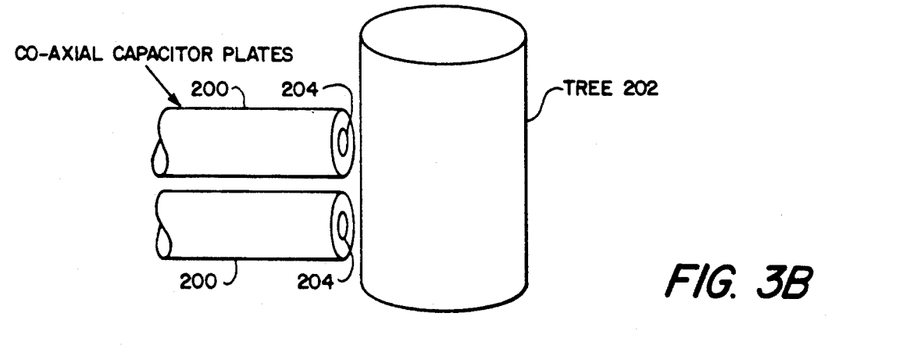
FIG. 3B is a schematic drawing of the device of the invention wherein coaxial capacitor plates 200 are positioned on the same side of the plant 202 protected by coaxial guard plates (rings) 204.

The capacitor plates may be mounted on the same "side" of the plant as shown in FIG. 3.

The ideal relationship between oscillator frequency ($\nu$) and capacitance (C) is:

$$\nu = [RC \ln 4]^{-1} \quad (2)$$

Because the CFC circuit deviates from equation (2) for frequencies above approximately 40 kHz, the circuit was calibrated from 3 kHz to 120 kHz by placing a series of test capacitors (11 to 1100 pF) across the terminals of the CFC and measuring the frequency. The frequencies for the CFC circuit when placed around a palm stem were in the range of 40 to 70 kHz. For the calibration, oscillator frequency was measured using a high-precision stabilized counter (Model 5385A, Hewlett-Packard, Inc.). The test capacitors were measured with a capacitance meter (Beckman Circuitmate DM25L), accurate to 3%. Interpolation of frequency data into capacitance was performed by fitting the calibration data for the CFC circuits to a log power series:

$$\log_{10}(C) = \sum_{i=0}^{n} A_i [\log_{10}(\nu)]^i \quad (1)$$

where n = 1 to 4, $r^2 > 0.999$.

Because of the high input impedance of the timing capacitor (infinite in the real part), it was necessary to guard the circuit to eliminate the capacitance of the coaxial cables (RG-58, 33 pF/ft), as well as any other capacitive couplings of the plates to objects other than the tree. Circuit board traces, coaxial cables leading to and from the tree, and the plates themselves, were guarded by surrounding them with a shield of equal potential. The guards consisted physically of a) external traces on the circuit board, b) the braided exterior portion of the coaxial cables to the plates, and c) a larger capacitor (copper plates 13.3×38.1 cm) located 7.6 cm exterior to the timing plates (FIG. 1). These were held at the same potential as the positive timing plate using an operational amplifier (LM310) configured as a unity gain follower. This chip has an extremely high input impedance ($10^{12}\Omega$, 1.5 pF) and thus has little influence on the resonant frequency. The circuit board was configured so that the LM310 input was also guarded, thus eliminating most of the 1.5 pF input capacitance. Low output impedance, on the other hand, allows the LM310 to supply sufficient current to hold the guard at the positive-plate potential.

It will also be understood by those skilled in the art that it is not critical to the invention to employ the LM310 amplifier. Any op-amp which can be configured as a unity gain follower may be employed in the practice of the invention.

Absence of fringing fields from the inner plates, a direct consequence of the guard plates, allows the dielectric constant ($\epsilon$) of the material between the timing plates to be calculated to a high degree of accuracy using the ideal parallel plate capacitor formula:

$$\epsilon = Cd/A\epsilon_o \quad (4)$$

where C is the measured capacitance (F), d is the distance between the plates (m), A is the area of the plates (m$^2$), and $\epsilon_o$ is the relative permitivity of free space ($8.85\times10^{-12}$ F/m). Thus, if water is withdrawn from stem tissues during the day by transpiration, the dielectric constant should decrease causing the value of the timing capacitor to decrease and the oscillator frequency to increase. Recharge of stem tissue during the night as water is drawn from the soil should lead to an increase in the value of the apparent dielectric constant of the stem, resulting in an increase in the value of the timing capacitor and a decrease in the resonant frequency.

To avoid any systematic errors that might occur from differences in placement or orientation of the capacitor plates on the tree (e.g., the degree to which they lie flush against the rough stem surface), measured $\epsilon$ was normalized by dividing it by the long-term mean value ($<\epsilon>$). In order to compare the relative magnitudes of diurnal fluctuations, the data were expressed as $[(\epsilon_{max} - \epsilon_{min})/<\epsilon>]$.

Several tests were conducted to determine the CFC sensitivity to changes in stem water content relative to changes in temperature. For these tests, the timing capacitor was placed across a glass aquarium in the laboratory and the CFC frequency and water temperature recorded. The dielectric constant of water was determined assuming that the copper plates sandwiched three homogeneous layers (glass-water-glass) and using published values for the dielectric constant of glass [Wheast, supra]. In addition, two water-filled plastic cylinders (1 m tall×0.25 m diameter) were used as "palm stem-analogues" in the greenhouse. These were used to assess the influence of fluctuations in air temperature on the measured dielectric constant of a uniform "stem" that was not changing in water content. Pure water was chosen because the relationship between temperature and $\epsilon$ is well known [Wheast, supra].

Changes in conductivity within the stem (e.g., resulting from changes in solute concentrations) were not anticipated to influence significantly measurements of stem capacitance because the circuit, by charging the plates with a constant amplitude ac voltage (peak to peak of $\frac{1}{3}V_{cc}$), resonates when the displacement current through the plates is maximum rather than when the charge on the plates is maximum. Nevertheless, CFC sensitivity to ion concentrations was tested using distilled water and a saturated salt solution. The "test cell" consisted of a 5.2×5.0×10.0 cm plastic container that was surrounded by the timing capacitor and filled with either deionized water or a saturated NaCl solution and the resonant frequency determined. These measurements were made in the laboratory at constant temperature.

CFC measurements of the dielectric constant of water made in the laboratory were close to published values [Wheast, supra]. The dielectric constant of 15° C. water in a glass aquarium (plate separation of 15.5 cm) was calculated to be 80.8±1.5 as compared to the published value of 82.0 [Wheast, supra]. The temperature dependence of these measurements was $-0.47\pm0.017°$ C.$^{-1}$, while the published data indicates a decrease in the dielectric constant of pure water of $-0.37°$ C.$^{-1}$ [Wheast, supra]. Uncertainty in these calculations derive from knowing neither the dielectric constant of the specific glass used in the aquarium, nor its temperature dependence; thus, the extreme values published for standard glass (6.32 to 6.75) [Wheast, supra] were used.

The dielectric constant of water-filled plastic cylinders in the greenhouse oscillated diurnally. The response to temperature was not the result of a direct effect on the electronics. The manufacturer's specifications for the timer chip and other components indicate a temperature sensitivity for the CFC circuit of less than 75 ppm °C.$^{-1}$, which corresponds to less than 4 Hz °C.$^{-1}$ for a circuit resonating at 50 kHz. This was confirmed by the lack of frequency oscillations when a fixed capacitor was placed across the terminals of the CFC in the greenhouse.

Figure 4:
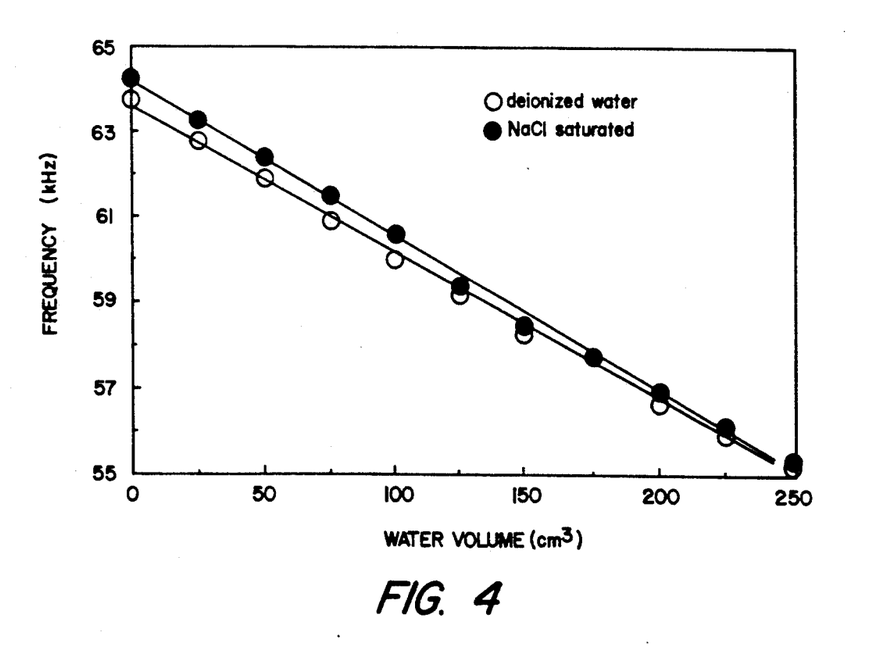
FIG. 4 is a depiction of the oscillator frequency as a function of the amount of water contained in a 250 cm$^3$ test cell. Measurements were made with deionized water (Y=63.573−0.0339X, r$^2$=0.998) and a saturated NaCl solution (Y=64.155−0.0359X, r$^2$=0.999).

Measurements confirmed that the CFC wa relatively insensitive to the presence of dissolved NaCl in pure water (FIG. 4). Resonant frequencies of the two liquids differed most at low water volumes (i.e., when the test cell was only partially full) and converged as the container filled.

Figure 5:
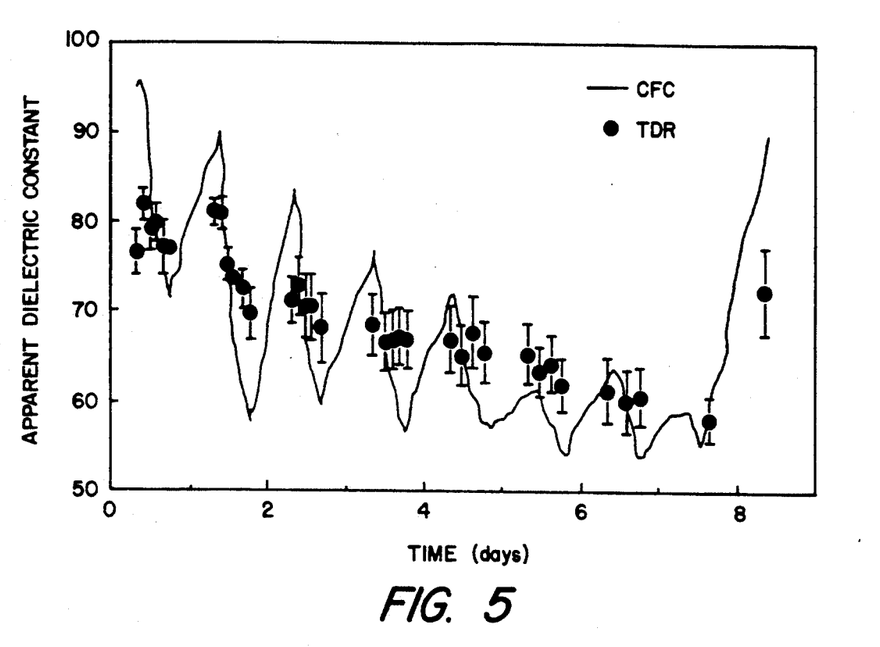
FIG. 5 is a depiction of the apparent dielectric constant of a palm stem as measured by capacitance-to-frequency converter (CFC) and time-domain reflectometry (TDR) techniques. The palm was initially well-watered. Water was withheld until the end of day seven at which time the plant was liberally watered.

The apparent dielectric constants ($\epsilon_{apparent}$) of palm stems as measured by the CFC were within the range of values expected for a partially saturated medium (40 to 70, FIG. 5). The $\epsilon_{apparent}$ of a palm tree from which water was withheld for two successive seven-day periods showed three patterns: 1) a daily oscillation in $\epsilon_{apparent}$; 2) a decrease in the mean daily value as water was withheld, and 3) a decrease in the amplitude of the diurnal fluctuations as water was withheld. Addition of water to the pot at the end of the seven-day drying period reversed the latter two trends. The apparent dielectric constant of the stem decreased during the daylight hours with daily minima being reached at approximately 1900 EST and increased throughout the night (maxima at approximately 0900 EST). These patterns are in accord with the hypothesis that water is extracted from the stem to meet both short-term (daily) and long-term transpiration-induced deficits.

Figure 6:
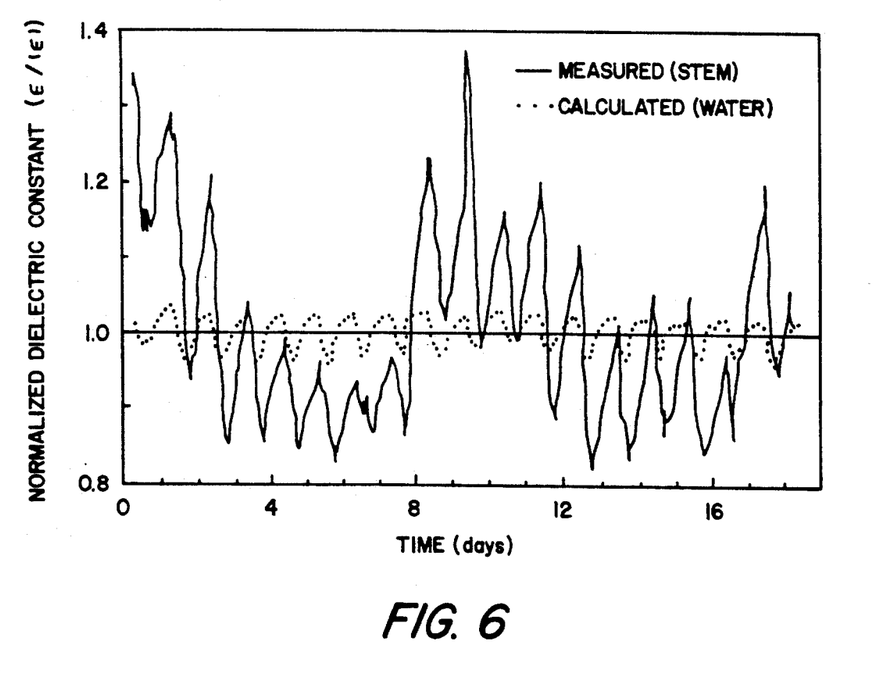
FIG. 6 depicts measured and calculated values of the apparent dielectric constant of palm stems normalized by the main $<\epsilon>$ to remove any systematic error. The palm was initially well-watered and water was added on days seven, nine and sixteen. The calculated values illustrate what the device would indicate if the measured effects were due to temperature variations of the tree.

Daily variations in temperature could also result in diurnal oscillations in $\epsilon_{apparent}$ (i.e., minimia in the afternoon, maxima in the morning). Diurnal oscillations in the dielectric constant of pure water calculated from measurements of air temperature, however, were smaller than those of the stem material (FIG. 6). Furthermore, unlike the diurnal fluctuations in $\epsilon_{apparent}$ of the stem, there was no change in either the range or the amplitude of $\epsilon_{pure\ water}$ calculated from air temperature. The relative diurnal fluctuation [$(\epsilon_{max}-\epsilon_{min})/<\epsilon>$] of the stem was between 0.30 and 0.35 when the tree was maximally transpiring, while values between 0.13 and 0.18 were characteristic of days later in the drying period. In contrast, the mean relative diurnal fluctuation of $\epsilon_{pure\ water}$ calculated from air temperature was 0.058. These data indicate that the patterns of $\epsilon_{apparent}$ of the stem cannot be fully accounted for by the effects of temperature on the dielectric constant of pure water. They do not, however, rule out an interaction between temperature and $\epsilon_{apparent}$ of a complex, living tissue [Pethig, *Dielectric and Electric Properties of Biological Materials*, John Wiley & Sons, Chichester (1979)].

Water loss from a tree was prevented in one test by enclosing the entire leaf crown in a large bag of aluminized mylar. Diurnal fluctuations in $\epsilon_{apparent}$ were also observed in this stem which was not losing water by transpiration. Relative diurnal fluctuation in $\epsilon[(\epsilon_{max}-\epsilon_{min})/<\epsilon>]$ of the mylar-enclosed tree was 0.150, while changes in air temperature during these measurements were estimated to result in a relative fluctuation in $\epsilon_{pure\ water}$ of 0.068. Cut lengths of stem (1.2 m long) from recently felled trees also exhibited diurnal fluctuations in $\epsilon_{apparent}$. Stem sections located both within the laboratory and outdoors had relative diurnal oscillations larger than that calculated for pure water tracking the ambient temperature (Table 1). The relative fluctuation in $\epsilon_{apparent}$ of the stem segment located outdoors was over twice that of the stem segment in the laboratory, while the calculated fluctuations of $\epsilon_{pure\ water}$ attributable to temperature variations increased by approximately 3.5 (Table 1).

Time-domain reflectometry (TDR) measurements of the apparent dielectric constant of excised stem sections in the laboratory were related to the volumetric water content although the variance was high. Possible sources of error included tissue damage caused by handling and rod insertion, uneven distribution of moisture throughout the tissue as it dried, and changes in tissue volume as it dried. Sectioning of the palm stems did not indicate tissue damage because tissue discoloration was slight and restricted to within 2 mm of the rods. Tissue drying did not result in detectable changes in the spacing of the wave guides, although it influenced calculation of the volumetric water content. A similar dependence of $\epsilon$ on the moisture content of tropical vegetation samples was seen by Tan ["Microwave measurements and modelling of the permitivity of tropical vegetation samples," *Applied Physics*, Vol. 25, pages 351–355 (1981)] using microwave measurements at 9.5 GHz.

TABLE 1

CFC Measurements of the Dielectric Constant of Stem Segments ($\epsilon_{stem}$) Located in the Laboratory and Outdoors The cut ends of each segment were covered to prevent water loss. Air temperature ($T_{air}$, °C.) was measured in each location and the dielectric constant of pure water at that temperature calculated ($\epsilon_{water}$). Values represent the mean (se) of parameters from three one-day intervals ($\bar{X}$). Diurnal fluctuation (DF) refers to the amount each parameter (temperature or measured dielectric constant) varied within a day; relative diurnal fluctuation (RDF) is the normalized fluctuation in the dielectric constant [$(\epsilon_{max}-\epsilon_{min})/<\epsilon>$].

|  | Laboratory | | | Outdoors | | |
|---|---|---|---|---|---|---|
|  | $T_{air}$ | $\epsilon_{stem}$ (measured) | $\epsilon_{water}$ (calculated) | $T_{air}$ | $\epsilon_{stem}$ (measured) | $\epsilon_{water}$ (calculated) |
| $\bar{X}$ | 23.3 | 57.1 | 78.9 | 18.3 | 64.0 | 80.8 |
|  | (0.28) | (1.35) | (0.10) | (1.85) | (0.73) | (0.68) |
| DF | 3.2 | 3.0 | 1.2 | 14.1 | 9.4 | 5.2 |
|  | (0.16) | (0.59) | (0.06) | (1.18) | (1.94) | (0.44) |
| RDF |  | 0.064 | 0.015 |  | 0.146 | 0.054 |
|  |  | (0.005) | (0.001) |  | (0.029) | (0.012) |

We claim:

1. A device for the non-invasive monitoring of the hydration state of a plant comprising the elements:

a timing capacitor comprising a plurality of conductive elements adapted for mounting on a plant part to sense the hydration state capacitance of said plant part;

a capacitance-to-frequency converter electrically connected to said timing capacitor comprising an oscillator circuit having a frequency dependent upon the value of said timing capacitor and independent of the electrical losses in said timing capacitor;

means for supplying electrical power to said capacitance-to-frequency converter;

means for measuring the frequency generated by said capacitance-to-frequency converter, said frequency bearing a known relationship to the dielectric constant and, hence, the water content of said plant part; and devices for electrically guarding the circuit generated by said elements from capacitance extraneous to said plant part comprising means for surrounding said element with shields of electrical potential substantially equal to that of the timing capacitor.

2. The device of claim 1 wherein said timing capacitor comprises a pair of electrically conductive plates adapted for mounting on the opposite sides of a tree stem or trunk.

3. The device of claim 1 wherein said capacitance-to-frequency converter is a relaxation oscillator wherein its frequency varies in a known way with the capacitance of the timing capacitor.

4. The device of claim 3 wherein said capacitance-to-frequency converter comprises a current resonating circuit.

5. The device of claim 4 wherein said current resonating circuit is based on a timer chip.

6. The device of claim 1 wherein the circuit created by the elements of the monitoring device are protected against extraneous capacitance by a guard circuit based on an operational amplifier which surrounds said circuit with a shield of electrical potential equal to that of the timing capacitor.

7. The device of claim 6 wherein said amplifier is configured as a unity gain follower.

8. The device of claim 7 wherein said amplifier is an op-amp.

9. The device of claim 1 wherein said power supply means is adapted to supply a fixed voltage and the frequency of the capacitor-to-frequency converter is allowed to vary such that said circuit remains in resonance.

10. The device of claim 1 wherein said capacitor-to-frequency converter measures the current through said timing capacitor.

11. The device of claim 1 additionally including internal means for regulating the voltage to provide immunity to drifts and to shut-down operation of the device when the external power supply drifts below a predetermined value.

* * * * *